US011320383B2

(12) United States Patent
Jasper et al.

(10) Patent No.: US 11,320,383 B2
(45) Date of Patent: May 3, 2022

(54) METHOD FOR THE DETERMINATION OF FILM FORMING AMINES

(71) Applicant: KURITA WATER INDUSTRIES LTD., Tokyo (JP)

(72) Inventors: Julia Jasper, Krefeld (DE); Kirstin Zimmer, Solingen (DE); Andre De Bache, Langenfeld (DE); Wolfgang Hater, Kaarst (DE)

(73) Assignee: KURITA WATER INDUSTRIES LTD., Tokyo (JP)

( * ) Notice: Subject to any disclaimer, the term of this patent is extended or adjusted under 35 U.S.C. 154(b) by 158 days.

(21) Appl. No.: 16/497,801

(22) PCT Filed: Mar. 12, 2018

(86) PCT No.: PCT/JP2018/009406
§ 371 (c)(1),
(2) Date: Sep. 26, 2019

(87) PCT Pub. No.: WO2018/180408
PCT Pub. Date: Oct. 4, 2018

(65) Prior Publication Data
US 2021/0123867 A1    Apr. 29, 2021

(30) Foreign Application Priority Data
Mar. 28, 2017  (EP) ..................... 17163345

(51) Int. Cl.
*G01N 21/78* (2006.01)
*G01N 1/40* (2006.01)
*G01N 33/18* (2006.01)

(52) U.S. Cl.
CPC .............. *G01N 21/78* (2013.01); *G01N 1/405* (2013.01); *G01N 1/4077* (2013.01); *G01N 33/18* (2013.01); *G01N 2001/4088* (2013.01)

(58) Field of Classification Search
CPC ...... G01N 21/78; G01N 1/405; G01N 1/4077; G01N 33/18; G01N 2001/4088; G01N 31/22
See application file for complete search history.

(56) References Cited

U.S. PATENT DOCUMENTS

| 5,248,494 A * | 9/1993 | Kuleza ................. A61K 9/0014 424/45 |
| 5,858,798 A | 1/1999 | Godfrey et al. |
| 2012/0028297 A1* | 2/2012 | Zook ....................... G01N 1/02 435/39 |
| 2016/0091469 A1* | 3/2016 | Lendi ................... G01N 21/253 436/85 |

FOREIGN PATENT DOCUMENTS

| GB | 994051 | 6/1965 |
| JP | S63302980 | 12/1988 |
| JP | H0514736 | 2/1993 |
| JP | H066643 | 1/1994 |
| JP | H11124771 | 5/1999 |
| JP | H11323579 | 11/1999 |
| JP | 2001510572 | 7/2001 |
| JP | 2002504678 | 2/2002 |
| JP | 2003528186 | 9/2003 |
| JP | 2008116280 | 5/2008 |
| JP | 2008249573 | 10/2008 |
| JP | 2008279573 | 11/2008 |
| JP | 2011513741 | 4/2011 |
| JP | 2015175551 | 10/2015 |

OTHER PUBLICATIONS

Gridchin, A. A., O. N. Mozharenko, and A. É. Popov. "New Amine Water Treatment at the Vaz TPP." Power Technology and Engineering 50.3 (2016): 323-328. (Year: 2016).*
"International Search Report (Form PCT/ISA/210) of PCT/JP2018/009406," dated May 22, 2018, pp. 1-2.

* cited by examiner

*Primary Examiner* — Jennifer Wecker
*Assistant Examiner* — Oyeleye Alexander Alabi
(74) *Attorney, Agent, or Firm* — JCIPRNET

(57) ABSTRACT

The present invention relates to a method for the determination of the film forming amines on surfaces by the detection of a colored complex. The invention also relates to the use of the absorber material for the detection of the film forming amines. The invention also relates to a kit of parts comprising the components capable of the determination of film forming amines.

21 Claims, No Drawings

METHOD FOR THE DETERMINATION OF FILM FORMING AMINES

CROSS-REFERENCE TO RELATED APPLICATION

This application is a 371 application of an international PCT application serial no. PCT/JP2018/009406, filed on Mar. 12, 2018, which claims the priority benefit of Europe application no. 17163345.6, filed on Mar. 28, 2017. The entirety of each of the above-mentioned patent applications is hereby incorporated by reference herein and made a part of this specification.

FIELD OF THE INVENTION

The present invention relates to a method for the determination of film forming amines on surfaces by the detection of a colored complex. The invention also relates to the use of an absorber material for the detection of the film forming amines. The invention also relates to the use of a test coupon for the detection of the film forming amines. The invention also relates to a kit of parts comprising the components capable of the determination of film forming amines.

BACKGROUND OF THE INVENTION

Water-bearing systems, in particular water circuits and steam circuits of steam generators, e.g. steam generators in electrical power plants, require water treatment additives in order to prevent damage of the surfaces in contact with water by corrosion or scaling.

Organic water additives based on film forming amines provide an excellent treatment for water/steam cycles. This holds especially for plants operating in cycle mode where preservation is required during shutdowns and protection of the parts both in contact with water and in dry state must be maintained. Film forming amines are characterized in that they bear at least one long-chain alkyl- or alkenyl group. The film forming amines form a protective layer between metal or metal oxide surfaces and the corrosive medium. The control of the effectiveness of the treatment so far is done by measurement of residual film forming amines in the water phase of the water cycle or the condensate of the water-steam cycle only, which is taken as an indirect proof of the complete protection of the surfaces. However, there is a demand for direct proof of the film forming amines on the different surfaces of the water-steam cycle, such as on turbine blades, on the inner drum surfaces.

The hydrophobicity of surfaces as it shows by water spraying can be used in order to qualitatively evaluate the presence of film forming amines on a surface. The test for hydrophobicity or droplet test is very simple and easy to apply. In case of a hydrophobic surface, the droplets have a typical round shape. The hydrophobicity can be quantified by contact angle measurement. However, this method is not suitable for plant inspections (Pensini, E., Cuoq, F., van Lier, R., Hater, W., Kraft, P., Halthur, T.: Laboratory Investigations for the Replacement of Cyclohexylamine by 2-(Diethylamino)ethanol in Film Forming Amine Product Formulations; Proceedings of the JIE 2016, Poitiers, to be published). In particular, this test does not always show hydrophobicity, especially on surfaces with porous materials, e.g. iron oxide layers, or on rough surfaces. Furthermore, this test is not selective for film forming amines.

WO 03/036260 relates to 1-hydroxybenzotriazole-6-carboxylic acid (HOBT) which is linked to a support which is a polymer. The immobilized HOBT can be used for derivatization of amines or modification of amines via acylation reaction or sulfonylation reaction in order to detect and separate the amines. This document relates to a method for determining amines that are different from the amines according to the invention having at least one linear or branched acyclic $C_{12}$-$C_{22}$ hydrocarbon group.

US 2006/057022 relates to a method for determining microbial food spoilage. Foods may contain amounts of proteins or amines. A presence of amines can be detected by xanthene dyes, azo dyes or hydroxyl-functional triphenylmethane dyes. The detected amines are selected from putrescin (butane-1,4-diamine), cadaverine (pentane-1,5-diamine), histamine (2-(1H-imidazol-4-yl)ethanamine), ammonia, dimethylamine, trimethylamine, indoles, spermine and spermidine.

WO 2006/079167 relates to a device for testing the presence of an analyte which is selected from nitroaromatics, nitroamines, nitrate esters or oxidisers. However, the determination of amines according to the invention is not mentioned.

GB 994 051 relates to the determination of amines in water, for example boiler feed water, steam condensate and cooling water. The concentration of the amines in water is detected by an indicator which is a compound of the sulphonaphthalein class.

Accordingly, it is an object of the present invention to provide a simple and selective method for the determination of at least one film forming amine on the surfaces qualitatively and quantitatively to ensure a complete film formation. The test should be applicable during plant inspection without the need of taking surfaces samples, e.g. tube cutting.

SUMMARY OF THE INVENTION

Surprisingly, the problem underlying the invention is solved by a method of determining whether a surface contains a protective amount of at least one film forming organic amine having at least one linear or branched, acyclic hydrocarbon group having 12 to 22 carbon atoms, the method comprising taking a sample from the surface and analyzing the sample for the presence of the least one film forming organic amine.

The method according to the invention and the special embodiments thereof described hereinafter is advantageous with respect to one or more of the following points:
- The evaluation is possible directly on site and without great technical effort.
- The method of the invention is a direct test for the existence/non-existence of a protective layer on the surface using color reagents or fluorescent substances.
- The method is sensitive for low concentrations of film forming amines.
- The method leads to clearly visible coloration and thus is suitable for a simple application. In the simplest case detection of the presence of a protective layer of the film forming amine on the surface can be done by the bare eye.
- The method is not negatively affected by iron oxide and its color.
- The method uses only safe chemicals.
- The method also allows quantitative measurements of the film forming amines.

The method can be performed indirectly for the determination of the presence of film forming amines in the water by using a test coupon, which is incorporated in the in the water cycle or steam cycle.

The test coupon is easy accessible and can be changed easily.

The invention also relates to the use of an absorber material selected from cellulose, modified celluloses and polyvinylidene fluoride (PVDF) for the detection of the film forming amines.

The invention also relates to the use of a test coupon, which is incorporated in the water cycle or steam cycle for a sufficient time, in order to allow the deposition of the film forming amines on the surface of the test coupon. After removal of the test coupon laden with the film forming amines, the surface of the test coupon is examined by the method described above and below for the detection of the film forming amines.

The invention also relates to a kit of parts comprising the capable components for the determination of film forming amines.

DETAILED DESCRIPTION OF THE INVENTION

It was now surprisingly found that it is possible to detect by a direct test whether on the surface of a certain object, in particular the surface of a water/steam cycle structure, exists a protective layer of at least one film forming amine or not. It was found that there is a good correlation between complete film formation on all surfaces of a water/steam cycle and the determination of the film forming amine in a sample taken directly from said surfaces. In particular, it is possible to take a surface sample under standardized conditions and perform a simple color reaction that allows judging the existence/non-existence of a protective layer of at least one film forming amine with the bare eye. According to the process of the invention it is in particular possible to perform a simple standardized test by bringing a surface into intimate contact with an absorber material to effect a transfer the film forming amine to the absorber material, release the amine from the loaded absorber material by extraction with a solvent and adding a reagent capable to form a colored complex with the film forming amine to the extract. If the formation of a colored complex occurs, the surface contains a sufficient amount of film forming amine. In a special embodiment the surface is brought into contact with a preconditioned wipe, extracted with a predefined amount of a solvent and a predefined amount of color forming reagent like bengale rosa is added. The occurrence of a colored complex indicates sufficient protection of the surface. In another embodiment, a test coupon, which previously has not been exposed to any film forming amines or film forming amines containing water or water containing film forming amines, is incorporated into a suitable position inside the water/steam cycle with water flow. After a sufficient time, which allows the deposition of the film forming amines on the surface of the test coupon, the test coupon is removed from the water/steam cycle. The surface of the test coupon is extracted by washing the surface with a solvent and adding a reagent capable to form a colored complex with the film forming amine to the solvent comprising the film forming amine. If the formation of a colored complex occurs, the surface contains a sufficient amount of film forming amine.

According to the process of the invention the existence of a protective amount of at least one film forming organic amine means that the film forming organic amine forms a colored complex with a reagent. Accordingly, the film forming amines form a protective layer between a metal or metal oxide surface and a corrosive medium, e. g. oxygen, carbon dioxide, carbonic acid etc. In case the film forming organic amine and the reagent form a colored complex this means the presence of a sufficiency amount of film forming organic amine to protect the metal or metal oxide surfaces. In case the film forming organic amine and the reagent do not form a colored complex means either the amount of the film forming organic amine is too low for forming a protective layer or the film forming organic amine is completely absent. Thus, the test is negative and no protective layer exists between the metal or metal oxide surface and the corrosive.

In the sense of the invention taking a sample from a surface means that the sample can be taken at a time the surface is free to access, e.g. in case of a water-steam cycle during standstill or outages, e. g. during plant inspection. There is no need of damaging the surface, e.g. by taking surface samples by destructive methods like tube cutting.

In a preferred embodiment of the invention for taking the sample an absorber material is brought into intimate contact with the surface to transfer the at least one organic amine as defined above and below and preferably of the formula (I) to the substrate.

In another embodiment the surface of a test coupon, is analyzed for the presence of the least one film forming organic amine as defined above and below and preferably of the formula (I).

In the sense of the invention the terms absorber material and substrate are used synonymously.

In the sense of the invention surfaces means all surfaces which may generally protected by at least one layer of the film forming organic amine.

In a further preferred embodiment of the invention the surface is a water or steam contacted surface of a water cycle or steam cycle. Generally, water cycle or steam cycles can be found in plants. In a special embodiment the surface of turbine blades or the inner or outer drum surfaces of water or steam contacted surface are used.

In another embodiment of the invention a test coupon is incorporated inside the water cycle or steam cycle for a sufficient time to absorb the at least one organic amine as defined above and below present in the a water cycle or steam cycle.

In the sense of the invention the term sufficient time means the time that it takes for depositing an amount of the at least one organic film forming amine on the surface of the test coupon that is representative for the amount of the at least one organic film forming amine on the water or steam contacted surface of the water cycle or steam cycle. It is the time it takes to reach a steady state (equilibrium) between the amount of the at least one organic film forming amine on the surface of the test coupon and the amount of the at least one organic film forming amine on the surface of the water cycle or steam cycle.

Generally the time the test coupon is incorporated inside the water or steam cycle is at least one week, preferably at least 2 weeks.

If for each measurement the period of installation is the same for each test coupon and the water flow rate is similar, the adsorption reading is a relative measure for the film forming amine concentration in the water. Therefore, the higher the reading, the higher the film forming amine concentration in the water.

In another preferred embodiment the test coupon is made of a material, which capable to absorb the at least one organic film forming amine as defined above and below. Preferably, the test coupon is made of a material, which is inert in the water/steam cycle and which is inert to the at least one organic amine. More preferably, the test coupon is made of a material, which is used in the water/steam cycle. Especially, the test coupon is made of steel, stainless steel or copper.

In the sense of the invention steel is an alloy of iron and carbon and other elements.

The carbon content of steel is between 0.002% and 2.14% by weight for plain iron-carbon alloys. These values vary depending on alloying elements such as manganese, chromium, nickel, iron, tungsten, carbon.

In the sense of the invention stainless steel is a steel alloy with a minimum of 10.5% chromium content by mass.

The test coupon principally can be installed in all places and positions of the water/steam cycle. Preferably, the test coupon is positioned into the samples lines of the water/steam cycle.

In principle, the shape of the test coupon is not critical. Thus it can e.g. have a rectangular, square or round shape. The surface area of the test coupon being in contact with water and/or steam when incorporated in the water or steam cycle is preferably in a range of from 5 mm$^2$ to 1 m$^2$, more preferably of from 10 mm$^2$ to 0.25 m$^2$.

In a preferred embodiment the amine is a compound of formula (I):

wherein
n is 0, 1, 2, 3 or 4,
$R^1$ is a linear or branched, acyclic hydrocarbon group having 12 to 22 carbon atoms,
$R^2$ is $C_1$-$C_4$-alkanediyl,
$R^3$, $R^4$, $R^5$ are independently H or $C_1$-$C_4$ alkyl or —$(C_mH_{2m-2}O)_p$—H, wherein m is 1, 2, 3, or 4 and p is =1, 2, 3 or 4.

In a further preferred embodiment the method according to the invention comprises the addition of a reagent capable to form a colored complex with the at least one organic amine of the formula (I) as defined above and below and detecting the colored complex.

A further preferred embodiment of the invention is a method for the determination of at least one organic amine of the formula (I)

wherein
n is 0, 1, 2, 3 or 4,
$R^1$ is a linear or branched, acyclic hydrocarbon group having 12 to 22 carbon atoms,
$R^2$ is $C_1$-$C_4$-alkanediyl,
$R^3$, $R^4$, $R^5$ are independently H or $C_1$-$C_4$ alkyl or —$(C_mH_{2m-2}O)_p$—H, wherein m is 1, 2, 3, or 4 and p is =1, 2, 3 or 4,
on surfaces comprising the steps
i) transfer of the at least one organic amine of the formula (I) to the absorber material, which comprises a solvent a),
ii) extraction of the amine of the formula (I) out of the absorber material with a second solvent b), which is the same as or different from the solvent a) to obtain an extract comprising the solvent b), the at least one organic amine of the formula (I) and optionally the solvent a),
iia) optionally, filtration of the extract,
iii) optionally adjusting the pH-value of the obtained extract,
iv) adding a reagent capable to form a colored complex with the at least one organic amine of the formula (I),
v) detecting the colored complex.

In another embodiment of the invention is a method for the determination of at least one organic amine of the formula (I)

wherein
n is 0, 1, 2, 3 or 4,
$R^1$ is a linear or branched, acyclic hydrocarbon group having 12 to 22 carbon atoms, $R^2$ is $C_1$-$C_4$-alkanediyl,
$R^3$, $R^4$, $R^5$ are independently H or $C_1$-$C_4$ alkyl or —$(C_mH_{2m-2}O)_p$—H, wherein m is 1, 2, 3, or 4 and p is =1, 2, 3 or 4,
on surfaces comprising the steps
washing of the at least one organic amine of the formula (I) from the surface of the test coupon removed from the water cycle or steam cycle using a solvent c) to obtain an extract comprising the solvent c) and the at least one organic amine of the formula (I),
viia) optionally, filtration of the obtained extract,
viib) optionally, adjusting the pH-value of the obtained extract,
viii) adding a reagent capable to form a colored complex with the at least one organic amine of the formula (I),
ix) detecting the colored complex.

Of course the invention also encompasses that the organic amine absorbed on the test coupon can be transferred first to an absorber material as defined above followed by the extraction of the organic amine from the absorber material as described above. Reference is made by the aforementioned measures, which are incorporated to reference.

In the sense of the invention, the expression film forming amines refer to organic amines of the formula (I)

wherein, $R^1$, $R^2$, $R^3$, $R^4$, $R^5$ and n have one of the meanings as defined above or in the following.

In the context of formula (I), $R^1$ is preferably a linear, i.e. straight chain, hydrocarbon group having 12 to 22 carbon atoms, in particular a saturated linear hydrocarbon group having 12 to 22 carbon atoms or an unsaturated linear hydrocarbon group having 12 to 22 carbon atoms and 1, 2, 3 or 4 C=C-double bonds, in particular 1 or 2 C=C-double bonds. Preferably, $R^1$ has 16 to 20 carbon atoms. In particular, $R^1$ is a straight chain hydrocarbon group having 16 to 20 carbon atoms, especially a saturated straight chain hydrocarbon group having 16 to 20 carbon atoms or an unsaturated straight chain hydrocarbon group having 16 to 20 carbon atoms and 1 or 2 C=C-double bonds. Especially, $R^1$ is a straight chain hydrocarbon group having 18 carbon atoms, especially a saturated linear hydrocarbon group having 18 carbon atoms or an unsaturated straight chain hydrocarbon group having 18 carbon atoms and 1 C=C-double bond, especially preferred $R^1$ is an unsaturated straight chain hydrocarbon group having 18 carbon atoms and 1 C=C-double bond.

Examples of groups $R^1$ include, but are not limited to lauryl (n-dodecyl), myristyl (n-tetradecyl), cetyl (n-hexadecyl), margaryl (n-heptadecyl), stearyl (n-octadecyl), arachidyl (n-eicosanyl), behenyl (n-docosenyl), palmitoleyl (9-hexadecen-1-yl), oleyl(9-hexadecen-1-yl), 11-octadecen-1-yl, 9,12-octadecadien-1-yl and 9,12,15-octadecatrien-1-yl and mixtures thereof, such as tallowalkyl (mixture of linear alkyl which mainly consists of linear $C_{16}/C_{18}$ alkyl), and cocoalkyl (mixture of linear alkyl, which mainly consists of $C_{12}$-$C_{18}$-alkyl). In a very special embodiment, $R^1$ is oleyl, which means $C_{18}H_{35}$-radical.

In the context of formula (I), $C_2$-$C_4$-alkanediyl is understood to include a bivalent saturated hydrocarbon group having 2, 3 or 4 carbon atoms, which may be linear or branched and which is preferably linear. Hence, $R^2$ is ethanediyl, propanediyl or butanediyl. $R^2$ is in particular 1,2-ethanediyl or 1,3-propanediyl, and especially 1,3-propanediyl.

In the context of formula (I), $C_1$-$C_4$-alkyl denotes a linear or branched alkyl radical comprising from 1 to 4 carbon atoms, for example $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$. Hence, $R^3$, $R^4$ and $R^5$ are independently selected from hydrogen, $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$. In particular, $R^3$, $R^4$ and $R^5$ are independently selected from hydrogen $CH_3$, $C_2H_5$, n-propyl and $CH(CH_3)_2$, and especially hydrogen.

In the context of formula (I), n is preferably 0, 1 or 2, in particular 1.

Examples of particular amines of formula (I) with n being 0 are octadecylamine, oleylamine, tallowamine.

Examples of particular amines of formula (I) with n being 1 or 2 are N-oleyl-1,3-diaminoethane, N-tallow-1,3-diaminopropane, 1-cocoalkyl-1,3-diaminopropane, stearyl-1,3-diaminopropane, N-[3-(cocoalkylamino)propyl]propane-1,3-diamine (=cocoalkyldipropylentriamine), N-[3-(tallowalkylamino)propyl]propane-1,3-diamine (=tallowalkyldipropylentriamine), N-[3-[3-(cocoalkylamino)propylamino]propyl]propane-1,3-diamine (=cocoalkyltripropylentetramine) and N-[3-[3-(tallowalkylamino)propylamino]propyl]propane-1,3-diamine (=tallowalkyltripropylentetramine). Suitable amines of the formula (I) with n being 1 or 2 are commercially available, e.g. the Duomeen(trade mark) brands of AkzoNobel, such as Duomeen(trade mark) T, Duomeen(trade mark) O and Duomeen(trade mark) C, the Triameen(trade mark) brands of AkzoNobel, such as Triameen(trade mark) T and Triameen(trade mark) C, the Dinoram(trade mark) brands of Archem, such as Dinoram(trade mark) O, and Inipol(trade mark) DS.

Examples of particular amines of formula (I) with n being 3 are commercially available as the Tetrameen(trade mark) brands of AkzoNobel, such as Tetrameen(trade mark) T.

Examples of particular amines with formula (I), wherein $R^3$, $R^4$ and/or $R^5$ are —$(C_mH_{2m-2}O)_p$—H, wherein m is 1, 2, 3, or 4 and p is =1, 2, 3 or 4 are alkoxylated fatty amines.

Alkoxylated fatty amines can be prepared by common methods, e.g. from the reaction of the corresponding primary or secondary fatty amines with at least one alkylene oxide. If primary fatty amines are employed for the alkoxylation, the resulting products bear two polyether chains bound to the nitrogen atom. In a special embodiment, a fatty amine mixture based on natural fatty amines is employed for alkoxylation. Amines based on animal fat e.g. comprise a mixture of oleic amine, palmitic amine, stearic amine, myristic amine and linoleic amine. Suitable primary fatty amines are e.g. amines derived from tallow, coconut oil, soybean oil, palm kernel oil, oleyl amine, decyl amine, undecyl amine, dodecyl amine, tridecyl amine, tetradecyl amine, hexadecyl amine, octadecyl amine, and mixtures thereof. Suitable fatty amines for alkoxylation are commercially available, e.g. cocoamine as Ethomeen C/12, Ethomeen C/15, Ethomeen C/25, Berol 398 or tallowamine as Ethomeen T/12, Ethomeen T/12 LC, Ethomeen T/15, Ethomeen T/25, Ethoduomeen T/13, Ethoduomeen T/22, Ethoduomeen T/25 or oleylamine as Berol 302, Ethomeen O/12, Ethomeen O/12 LC, Ethomeen OV/17, Ethomeen OV/22. Suitable alkylene oxides for alkoxylation are ethylene oxide (EO), propylene oxide (PO), 1,2-butylene oxide, 2,3-butylene oxide and mixtures thereof.

A special embodiment are ethoxylated fatty amines, preferably selected from ethoxylated tallow amine, ethoxylated coco amine, ethoxylated soya amine, ethoxylated oleyl amine, ethoxylated decyl amine, ethoxylated dodecyl amine, ethoxylated tridecyl amine, and ethoxylated tetradecyl amine.

Preferred ethoxylated fatty amines are ethoxylated tallow amine with 3 to 15 EO, ethoxylated coco amine with 3 to 15 EO, ethoxylated oleyl amine with 3 to 15 EO, ethoxylated dodecyl amine with 3 to 15 EO, ethoxylated tridecyl amine with 3 to 15 EO, ethoxylated tetradecyl amine with 3 to 15 EO, ethoxylated hexadecyl amine with 4 to 15 EO, ethoxylated octadecyl amine with 3 to 15 EO, and mixtures thereof.

Examples of particular amines with formula (I) with n being 1 and $R^3$, $R^4$ and/or $R^5$ are hydroxyethyl are commercially available as the Etoduomeen T series from Akzo Nobel, such as Ethoduomeen T/13, Ethoduomeen T/22, Ethodumeen T/25. A particular example is tris(2-hydroxyethyl)-N-tallowalkyl-1,3-diaminopropane.

Examples of particular amines with formula (I) with n being 0 and $R^3$, $R^4$ and $R^5$ are hydroxyethyl are commercially available as the Ethomeen T series from Akzo Nobel, such as Ethomeen C/12, Ethomeen C/15, Ethomeen C/25, Ethomeen T/12, Ethomeen T/12 LC, Ethomeen T/15, Ethomeen T/25, Ethomeen O/12, Ethomeen O/12 LC, Ethomeen OV/17, Ethomeen OV/22.

Step i)

In step i) of the method according to the invention the at least one organic amine of the formula (I) is transferred to an absorber material, which comprises a solvent a).

The absorber material is an absorbing wipe material suitable for wiping different surfaces of the water-steam cycle, such as on turbine blades, on the inner drum surfaces. Furthermore, the absorber material is capable to adsorb at least one organic amine of formula (I).

The term "absorber" as used herein includes also fabric, paper as well as paperboard and refers to sheet-like, usually porous structures containing a web of cellulosic pulp fibers, such as fibers derived from hardwood trees, softwood trees, or a combination of hardwood and softwood trees. Optionally at least a portion of the fibers may be synthetic fibers and/or may be provided from non-woody herbaceous plants, e.g. hemp, jute, flax or sisal. Additionally, the absorber may include conventional additives, such as, for example, glass fibers, mineral fillers, sizing agents, retention aids, and strengthening polymers.

The absorber material is selected from cellulose, modified celluloses, polyvinylidene fluoride (PVDF).

The term "cellulose" as used herein refers to a linear long-chain polysaccharide of the general formula $(C_6H_{10}O_5)_n$ comprising (1-4)-linked 3-glucose moieties as repeating units $(C_6H_{10}O_5)$, with the variable n being the average number of repeating units. Cellulose is usually a natural product found in plant cell walls accompanied mainly by lignin and hemicellulose.

The cellulose included in the cellulose product used in the method of the present invention may include other hexose moieties besides β-glucose moieties as repeating units, such as β-galactose moieties or α-glucose moieties. Preferably, the cellulose of the cellulose product consist of at least 95%, more preferably of at least 98% and in particular of at least 99% of 3-glucose moieties, based on the total average number n of repeating units included in the cellulose. In addition, some or all of the repeating units of the cellulose may be derivatized for example by partial or complete etherification or esterification of its hydroxyl groups. However, according to a preferred embodiment of the present invention less than 10%, preferably less than 5% and in particular less than 1% of the hydroxyl groups of cellulose are derivatized.

In a preferred embodiment the absorber material is cellulose, wherein the amount of α-cellulose is at least 95%.

As mentioned above, some or all of the repeating units of the cellulose may be derivatized for example by partial or complete etherification or esterification of its hydroxyl groups. Suitable modified celluloses are cellulose esters and cellulose ethers, e.g. cellulose acetate, ethyl cellulose, hydroxypropylcellulose, hydroxypropylmethylcellulose and carboxymethylcellulose cellulose.

Suitable absorber materials are commercially available, e.g. from VWR International GmbH, Machery-Nagel GmbH & Co. KG, Satorius stedim, Merck milipore Lts. Generally, the absorber material comprises at least one solvent a). The solvent a) is capable to transfer the at least one organic amine of formula (I) to the absorber material.

The at least one solvent a) is preferably selected from mixtures of at least one water-miscible organic solvent with water, wherein the weight portion of the at least one water-miscible organic solvent is at least 80%, particularly preferably at least 90% based on the total weight of solvent a).

In a special embodiment, the at least one solvent a) does not contain water.

The at least one solvent a) comprises or consists of one or more organic solvents having a vapour pressure of maximum 45 hPa at 20° C., preferably a vapour pressure of maximum 10 hPa at 20° C.

The at least one water-miscible organic solvent is selected from isopropanol, propylene carbonate, ethyleneglycol and butanol. In particular, the at least one water-miscible organic solvent is selected from isopropanol and propylene carbonate.

In a preferred embodiment, the at least one solvent a) is a mixtures of water with isopropanol, wherein the weight portion of isopropanol is at least 80% particularly preferably at least 90% based on the total weight of solvent a). In a special embodiment, isopropanol does not contain water.

In another preferred embodiment, the at least one solvent a) is a mixtures of water with propylene carbonate, wherein the weight portion of propylene carbonate is at least 80%, particularly preferably at least 90% based on the total weight of solvent a). In a special embodiment, propylene carbonate does not contain water.

In another preferred embodiment, the absorber comprises a suitable amount of solvent a).

Step ii) or Step vi)

In step ii) of the method according to the invention the at least one organic amine of the formula (I) is extracted out of the absorber material with a second solvent b) which is the same or different from the solvent a) with the proviso that solvent a) excludes propylene carbonate.

In step vi) of the method according to the invention the at least one organic amine of the formula (I) is washed from the surface of the test coupon removed from the water cycle or steam cycle using solvent c).

In a preferred embodiment, solvent b) used in step ii) is selected from a mixture of water with at least one water-miscible organic solvent in a weight ratio of 70:30 to 90:10, preferably 75:25 to 85:15.

The at least one water-miscible organic solvent in solvent b) is preferably selected from isopropanol, ethanol, acetone, butanone ethylacetate, methylacetate, ethyleneglycol, butanol, solvent a) and mixtures thereof with the proviso that solvent a) excludes propylene carbonate. In particular, the solvent b) is solvent a) with the proviso that solvent a) excludes propylene carbonate.

In a particular preferred embodiment, the at least one solvent b) has a propylene carbonate content of <1% by weight, in particular <0.5% by weight, based on the total amount of the solvent b). In a very special embodiment, the at least one solvent b) does not contain propylene carbonate.

In a preferred embodiment, the solvent b) is a mixture of water with isopropanol, wherein the weight ratio of water: isopropanol is in the range of 70:30 to 90:10, preferably 75:25 to 85:15.

After the extraction of the organic amine of formula (I), an extract, comprising the solvent b), the at last one organic amine of formula (I) and optionally the solvent a) is obtained.

In a preferred embodiment, solvent c) used in step vi) is selected from a mixture of water with at least one water-miscible organic solvent in a weight ratio of 70:30 to 90:10, preferably 75:25 to 85:15.

The at least one water-miscible organic solvent in solvent c) is preferably selected from isopropanol, ethyleneglycol, butanol, ethanol, acetone, butanone ethylacetate, methylacetate, ethyleneglycol and mixtures.

In particular, the solvent c) is solvent b) (with the proviso that propylene carbonate is excluded).

In a particular preferred embodiment, the at least one solvent c) has a propylene carbonate content of <1% by weight, in particular <0.5% by weight, based on the total amount of the solvent c). In a very special embodiment, the at least one solvent c) does not contain propylene carbonate.

In a preferred embodiment, the solvent c) is a mixture of water with isopropanol, wherein the weight ratio of water: isopropanol is in the range of 70:30 to 90:10, preferably 75:25 to 85:15.

After the washing of the organic amine of formula (I) from the surface of the test coupon, an extract, comprising the solvent c) and the at last one organic amine of formula (I) is obtained.

Preferably, the extraction in step ii) is carried out without shaking. Preferably, the extraction in step ii) is carried out for at least one minute, preferably at least two minutes.

Preferably, the test coupon, removed from the water cycle or steam cycle, is brought into intimate contact with solvent c). In particular the test coupon, removed from the water cycle or steam cycle, is immersed into solvent c). The amount of solvent c) is chosen that the surface of the test coupon is sufficiently covered by the solvent c). The amount of solvent c) depends on the surface area of the test coupon.

Preferably, the washing in step vi) is carried out with shaking or in an ultrasonic bath. Preferably, the washing in step vi) is carried out for at least one minute, preferably at least two minutes.

Step iia) or Step viia)

The obtained extract of step ii) is optionally filtered in step iia).

The obtained extract of step vi) is optionally filtered in step viia).

The filter material is preferably selected from modified cellulose, polytetrafluoroethylene (PTFE), PVDF, polyamide, such as nylon, polyolefines, such as polypropylene (PP).

Suitable modified celluloses are cellulose esters and cellulose ethers, e.g. cellulose acetate, ethyl cellulose, hydroxypropylcellulose, hydroxypropylmethylcellulose and carboxymethylcellulose cellulose, preferably, cellulose acetate and cellulose esters.

In a preferred embodiment, the filter material is polytetrafluoroethylene (PTFE).

The pore size of the filter material in step iia) is preferably below 1 μm, in particular below 0.5 μm, preferably below 0.2 μm.

Preferably, the obtained extract of step ii) is filtered in step iia).

Step iii) or Step viib)

The pH-value of the obtained extract of step ii) or iia), comprising the solvent b), the at least one organic amine of formula (I) and optionally the solvent a) is optionally preferably adjusted to the range of 1.8 to 3.5, more preferably to the range of 2.3 to 3.0. The adjustment of the pH-value is carried out by at least one acid.

The pH-value of the obtained extract of step vi) or viia), comprising the solvent c) and the at least one organic amine of formula (I) is optionally preferably adjusted to the range of 1.8 to 3.5, more preferably to the range of 2.3 to 3.0. The adjustment of the pH-value is carried out by at least one acid.

It has been found favourable if the acid is an inorganic acid, an aqueous solution of an inorganic acid, an organic acid, or an aqueous solution of an organic acid. Particular examples of the inorganic or organic acid are nitric acid, sulphuric acid, hydrochloric acid, phosphoric acid, acetic acid, formic acid, citric acid. Particular preferred are weak organic acids, preferably acetic acid and citric acid.

Step iv) or Step viii)

In step iii), the extract comprising the solvent b), the at least one organic amine of formula (I) and optionally the solvent a), wherein the pH-value of the extract is preferably in the range of 1.8 to 3.5, more preferably in the range of 2.3 to 3.0 is obtained.

In step viia), the extract comprising the solvent c) and the at least one organic amine of formula (I), wherein the pH-value of the extract is preferably in the range of 1.8 to 3.5, more preferably in the range of 2.3 to 3.0 is obtained.

A reagent, which is capable to form a colored complex with the at least one organic amine of the formula (I) is added. The reagent is a compound comprising the Xanthene-type. In particular, the reagent is a compound of formula (II)

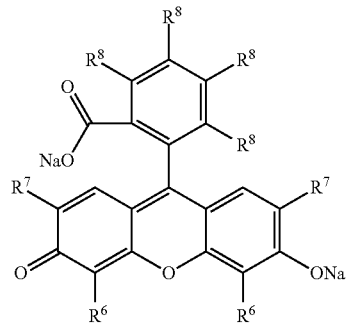

(II)

wherein
$R^6$ and $R^8$ are independently from each other H or halogen;
$R^7$ is selected from H, halogen and $NO_2$.

In a particular embodiment, the reagent is selected from Eosin B, Eosin Y, Erythrosine, Fluorescein and Bengal rose, wherein Bengal rose is preferred.

Generally, the compound (II) is employed in an amount at least equimolar to the amount of the organic amine of formula (I) in the extract.

A colored complex of the organic amine of formula (I) and the reagent, in particular of compound of formula (II) is formed.

Step v) or Step ix)

The obtained colored complex formed by the reagent and the organic amine of formula (I) is detected by photometric measurements. Suitable detectors are principally known to a person skilled in the art and are e.g. Fotometer DR6000, Hach Lange GmbH.

Photometric measurement is based on photodetectors, devices (of several types) that produce an electric signal when exposed to light. Simple applications of this technology include switching luminaires on and off based on ambient light conditions, and light meters, used to measure the total amount of light incident on a point.

The invention also relates to the use of the absorber material for the detection of the film forming amines.

It is also possible for the components of the inventive method to be packaged and used as combination composition, such as a kit of parts. Thus, the invention also relates to a kit of parts comprising the components capable of the determination of organic amines of formula (I).

In one embodiment of the invention, a kit of parts comprises, as separate components, the 1) absorber material, 2) solvent a), 3) solvent b), 4) filter material and 5) reagent for combined use. The kits may include one or more, including all, components that may be used to determine the organic amine of formula (I). It is also possible that the absorber material already comprises the solvent a). In those embodiments, where more than two components are provided in a kit, the components may already be combined together and as such are packaged in a single container, such as a vial, bottle, can, pouch, bag or canister. In other embodiments, two or more components of a kit may be packaged separately, i.e., not pre-formulated. As such, kits may include one or more separate containers, such as vials, cans, bottles, pouches, bags or canisters, each container containing a separate component for the determination of the organic amine of formula (I).

The invention also relates to the quantitative determination of the organic amines of formula (I) on surfaces, wherein the surface area is defined, comprising the steps i) transfer of the at least one organic amine of the formula (I) to an absorber material, which comprises a solvent a), ii) extraction of the amine of the formula (I) out of the absorber material with a second solvent b), which is the same as or different from the solvent a) to obtain an extract comprising the solvent b), the at least one organic amine of the formula (I) and optionally the solvent a), iia) optionally, filtration of the extract, iii) optionally adjusting the pH-value of the obtained extract, preferably to 1.8 to 3.5, more preferably in the range of 2.3 to 3.0, iv) adding a reagent capable to form a colored complex with the at least one organic amine of the formula (I), v) detecting the colored complex and detecting the concentration of the colored complex and vi) integrate the concentration and the defined surface area to determine the organic amine of formula (I) quantitatively, wherein the organic amine, the absorber material, solvent a), solvent b) are defined above.

The invention also relates to the quantitative determination of the organic amines of formula (I) on surfaces of the test coupon, wherein the surface area of the test coupon is defined, comprising the steps vii) washing of the at least one organic amine of the formula (I) from the surface of the test coupon removed from the water cycle or steam cycle using a solvent b), viiia) optionally, filtration of the solvent b) containing the at least one organic amine of the formula (I), viiib) optionally, adjusting the pH-value of the solvent b) containing the at least one organic amine of the formula (I), preferably to 1.8 to 3.5, more preferably in the range of 2.3 to 3.0, ix) adding a reagent capable to form a colored complex with the at least one organic amine of the formula (I), x) detecting the colored complex, xi) integrate the concentration and the defined surface area to determine the organic amine of formula (I) quantitatively, wherein the organic amine, solvent b) are defined above.

The invention is described in more detail by the following examples.

EXAMPLES

Analytik:
Fotometer Hach DR2500
General Procedure:

1. The absorber material, (3×6 cm) (Machery-Nagel GmbH & Co. KG, Duren: MN $616_{1/4}$, Cellulose), is wetted with a mixture of water and isopropanol solution, wherein the ratio isopropanol:water is 80:20.

2. The boiler/metal surfaces are wiped with this absorber material. The amines are absorbed on the surface of the absorber material.

3. The contaminated absorber material is put into a 10 ml syringe and 10 ml of the isopropanol solution is taken up with it, wherein the ratio isopropanol:water is 20:80.

4. The syringe is left with the orifice down in a beaker for two minutes without shaking.

5. A syringe filter (Minisart SRP 15 PTFE) is attached and the solution is pressed out of the syringe into a 25 ml 1-inch-round cuvette.

6. The reagent (bengal rosa, which is dissolved in e.g. butan-2-ol and a buffer solution, which is an aqueous solution consisting of a mixture of a weak organic acid, e. g. citric acid, acetic acid) is added, which is capable to form colored complexes with the organic amine. If the color becomes pink, the test is positive.

Test 1: Solvent Mixture: Isopropanol and Water
Calibration Procedure:

1. 2 g of the film forming amine was weighed in a 100 ml flask and filled up with isopropanol.

2. 0.1 ml of this solution was filled in a 100 ml flask with isopropanol.

3. Different volumes (0.125; 0.25; 0.5; 1; 2; 3; 3.75 ml) of the stock solution were filled in 25 ml 1-inch cuvettes, then the cuvette was filled with isopropanol until a certain volume (5 ml for a 20:80 solution, 3.75 ml for a 15:85 solution and 0 ml IPA for a 0:100 solution) and after that water was added to 25 ml.

4. The reagent (bengal rosa, which is dissolved in e.g. butan-2-ol and a buffer solution, which is an aqueous solution consisting of a mixture of a weak organic acid, e. g. citric acid, acetic acid) was added, and after 2 min the absorption was measured.

| Volume stock solution in the cuvette (ml) | Conc. film forming amine in the cuvette (mg/l) |
| --- | --- |
| 0.125 | 0.1 |
| 0.250 | 0.2 |
| 0.500 | 0.4 |
| 1.000 | 0.8 |
| 2.000 | 1.6 |
| 3.000 | 2.4 |
| 3.750 | 3.0 |

Isopropanol and water; blank value: solvent with reagents (bengal rosa, which is dissolved in e.g. butan-2-ol and a buffer solution, which is an aqueous solution consisting of a mixture of a weak organic acid, e. g. citric acid, acetic acid): 560 nm.

The film forming amine is oleylpropylenediamine (Dinoram O from Arkema Group).

The results of the absorption of the amine-reagent complexes at different solvent water mixtures are summarized in table 1. The procedure was performed in analogy as described above. The colored complex can be recognized with the bare eye.

TABLE 1

| ratio isopropanol:water | 20:80 | 15:85 | 10:90 | 0.004:99.996 |
| --- | --- | --- | --- | --- |
| conc. film forming amine (ppm) | Absorption | Absorption | Absorption | Absorption |
| 0.1 | 0.020 | 0.026 | 0.019 | 0.023 |
| 0.2 | 0.050 | 0.049 | 0.054 | 0.061 |
| 0.4 | 0.100 | 0.104 | 0.100 | 0.111 |
| 0.8 | 0.203 | 0.204 | 0.207 | 0.210 |
| 1.6 | 0.408 | 0.404 | 0.410 | 0.411 |
| 2.4 | 0.620 | 0.614 | 0.609 | 0.623 |
| cuvette: | 1 inch | 1 inch | 1 inch | 1 inch |

Test 2: In the Presence of Iron

Solution: 3.5 ppm oleylpropylenediamine with a micronized, yellowish iron oxide red pigment (Bayferrox 110M) in isopropanol Syringe: 10 ml (plastic)
Filter: white (PTFE; 0.45 μm) Satorius
Iron: Bayferrox 110M 1. Different solutions of oleylpropylenediamine with Bayferrox 110M were produced.

2. 5 ml of the produced solution was rinsed 3× through the syringe filter and the syringe.

3. Then the solution was transferred into a 25 ml 1-inch-round cuvette.

4. 20 ml deionized water and the reagents (bengal rosa, which is dissolved in e.g. butan-2-ol and a buffer solution, which is an aqueous solution consisting of a mixture of a weak organic acid, e. g. citric acid, acetic acid) were added. The absorption was measured with the photometer.

The results are summarized in table 2. Iron does not disturb the procedure.

TABLE 2

| Solution | Measured value [ppm oleylpropylenediamine] | Absorption |
| --- | --- | --- |
| oleylpropylenediamine + 1 ppm Fe | 3.5 | 0.177 |
| oleylpropylenediamine + 2 ppm Fe | 3.4 | 0.173 |
| oleylpropylenediamine + 5 ppm Fe | 3.2 | 0.162 |
| oleylpropylenediamine + 10 ppm Fe | 3.3 | 0.168 |
| oleylpropylenediamine + 20 ppm Fe | 3.4 | 0.174 |

Test 3: Different Surfaces

The surfaces of different metals (193.2 cm$^2$ (outside) and total surface of 347.8 cm$^2$ (inside and outside)) were treated with an aqueous solution comprising oleylpropylenediamine, tertiary ethoxylated amine, based on a primary tallow amine, monoethanolamine and diethylethanolamine, for 24 h. Then the procedure was performed in analogy as mentioned above. It was possible to detect on all surfaces oleylpropylenediamine.

The results for a copper surface (99.9% Cu, 0.015% P) are summarized in table 3.

TABLE 3

| Solution | Measured value [ppm oleylpropylenediamine] | Absorption |
| --- | --- | --- |
| ispropanol solution | 4.23 | 1.351 |

The results for a carbon steel surface (E235, No: 1.0308) are summarized in table 4.

TABLE 4

| Solution | Measured value [ppm oleylpropylenediamine] | Absorption |
| --- | --- | --- |
| ispropanol solution | 4.73 | 1.508 |

A Combined Cycle Gas Turbine (CCGT) design plant with Heat Recovery Steam Recovery Generator (HRSG) is operating the water-steam cycle with a chemical treatment based upon film forming amine (oleylpropylendiamine).

Steel coupons (Dimensions: 75×9.5×1.6 mm with a 5.5 mm hole, the middle of the short side; material: ST37 material code: 1.1010) were installed into several sampling lines of the plant. The test coupons exposed to plant conditions had been suspended in a sample container with a tube inserted to the container carrying the continuous sample flow for each sample point. The test coupons were removed for evaluation after having been exposed to the actual HRSG water sample flows at sampling temperature (25° C. and atmospheric pressure) for 5 weeks.

The removed test coupons were washed with 10 ml of the isopropanol solution, wherein the ratio isopropanol:water is 20:80. The reagent (bengal rosa, which is dissolved in e.g. butan-2-ol and a buffer solution, which is an aqueous solution consisting of a mixture of a weak organic acid, e. g. citric acid, acetic acid) is added, which is capable to form colored complexes with the organic amine. If the color becomes pink, the test is positive.

Table 5 shows the extention obtained with a standard fotometer (5 cm cuvette):

TABLE 5

| Coupon Position (sample point) | Time in sampling line | Extinktion |
| --- | --- | --- |
| Blank Coupon | n/a | 0.06 |
| Feedwater | 5 weeks | 0.78 |
| LP1 drum | 5 weeks | 0.21 |
| IP2 drum | 5 weeks | 0.16 |
| Condensate | 5 weeks | 0.14 |
| IP2 superheated steam | 5 weeks | 0.26 |

The invention claimed is:

1. A method of determining whether a water- or steam-contacted surface of a water cycle contains a protective amount of at least one film forming organic amine of formula (I) having at least one linear or branched, acyclic hydrocarbon group having 12 to 22 carbon atoms,

$$R^1-(NR^3R^2)_n-NR^4R^5 \qquad (I)$$

wherein n is 0, 1, 2, 3 or 4,

R$^1$ is a linear or branched, acyclic hydrocarbon group having 12 to 22 carbon atoms, R$^2$ is C$_1$-C$_4$-alkanediyl, R$^3$, R$^4$, R$^5$ are independently H or C$_1$-C$_4$ alkyl or —(C$_m$H$_{2m-2}$O)p-H, wherein in is 1, 2, 3, or 4 and p is =1, 2, 3 or 4, the method comprising:

an sampling step, wherein the surface is wiped with an absorber material, the organic amine is transferred to the absorber material, and the organic amine is taken from the surface, an extraction step, wherein a solvent is brought into contact with the absorber material and the organic amine is extracted into the solvent to obtain an extract containing the solvent and the organic amine, and an analysis step, analyzing the organic amine in the extract containing the solvent and the organic amine, on surfaces comprising the following steps:

vi) transfer of the at least one organic amine of the formula (I) from the water- or steam-contacted surface of a water cycle or steam cycle to the absorber material, which comprises a solvent a), vii) extraction of the amine of the formula (I) out of the absorber material with a second solvent b), which is the same as or different from the solvent a) to obtain an extract comprising the solvent b), the at least one organic amine of the formula (I) and optionally the solvent a), iia) filtration of the extract, viii) optionally, adjusting the pH-value of the obtained extract, ix) adding a reagent capable to form a colored complex with the at least one organic amine of the formula (I), x) detecting the colored complex.

2. The method according to claim 1, wherein in the sampling step, the surface is wiped with the absorber material wetted with a solvent the same as or different from the solvent used in the extraction step.

3. A method of determining whether a water- or steam-contacted surface of a water cycle or steam cycle contains a protective amount of at least one film forming organic amine of formula (I) having at least one linear or branched, acyclic hydrocarbon group having 12 to 22 carbon atoms, $$R^1-(NR^3R^2)_n-NR^4R^5 \quad (I)$$

wherein
n is 0, 1, 2, 3 or 4,
$R^1$ is a linear or branched, acyclic hydrocarbon group having 12 to 22 carbon atoms,
$R^2$ is $C_1$-$C_4$-alkanediyl,
$R^3$, $R^4$, $R^5$ are independently H or $C_1$-$C_4$ alkyl or —$(C_mH_{2m-2}O)$p-H, wherein m is 1, 2, 3, or 4 and p is =1, 2, 3 or 4,
the method comprising:
a contacting step, wherein a test coupon is incorporated inside the water cycle or steam cycle for a sufficient time to absorb the at least one organic amine of the formula (I) present in the water cycle or steam cycle, where the test coupon is made of a material which is capable to absorb the at least one organic amine,
a removing step, wherein the test coupon is removed from the plant,
an extraction step, wherein the test coupon is washed with a solvent and the organic amine is extracted to obtain an extract containing the solvent and the organic amine, and
an analysis step, analyzing the organic amine in the extract containing the solvent and the organic amine, and
on surfaces comprising the following steps:
vi) washing of the at least one organic amine of the formula (I) from the surface of the test coupon removed from the water cycle or steam cycle using a solvent c) to obtain an extract comprising the solvent c) and the at least one organic amine of the formula (I),
viia) filtration of the obtained extract,
viib) optionally, adjusting the pH-value of the obtained extract,
viii) adding a reagent capable to form a colored complex with the at least one organic amine of the formula (I),
ix) detecting the colored complex.

4. The method according to claim 3, wherein the test coupon is incorporated inside a water cycle or steam cycle for the sufficient time to absorb the at least one organic amine having at least one linear or branched, acyclic hydrocarbon group having 12 to 22 carbon atoms present in the water cycle or steam cycle.

5. The method according to claim 4, wherein the test coupon is made of a material, which is capable to absorb the at least one organic amine having at least one linear or branched, acyclic hydrocarbon group having 12 to 22 carbon atoms, or the test coupon is made of steel, stainless steel or copper.

6. The method according to claim 1, wherein the analysis step comprises the addition of a reagent capable to form a colored complex with the at least one organic amine of the formula (I) as defined in the preceding claims and detecting the colored complex.

7. The method according to claim 1, wherein the solvent a) used in step vi) is selected from mixtures of at least one water-miscible organic solvent with water, wherein the weight portion of the at least one water-miscible organic solvent is at least 80% based on the total weight of solvent a), or is at least 90% based on the total weight of solvent a).

8. The method according to claim 1, wherein, in step vi), solvent a) comprises or consists of one or more organic solvents having a vapour pressure of maximum 45 hPa at 20° C., or a vapour pressure of maximum 10 hPa at 20° C.

9. The method according to claim 7, wherein the at least one water-miscible organic solvent is selected from isopropanol, propylene carbonate, ethyleneglycol and butanol.

10. The method according to claim 1, wherein the solvent b) used in step vii) is selected from mixtures of water with at least one water-miscible organic solvent in a weight ratio of 70:30 to 90:10, or 75:25 to 85:15.

11. The method according to claim 10, wherein at least one water-miscible organic solvent in step vii) is selected from isopropanol, ethanol, acetone, butanone ethylacetate, methylacetate, ethyleneglycol, butanol, solvent a) and mixtures thereof, and the solvent b) is solvent a).

12. The method according to claim 3, wherein the solvent c) used in step vi) is selected from mixtures of water with at least one water-miscible organic solvent in a weight ratio of 70:30 to 90:10, or 75:25 to 85:15.

13. The method according to claim 12, wherein at least one water-miscible organic solvent in step vi) is selected from isopropanol, ethyleneglycol, butanol, ethanol, acetone, butanone ethylacetate, methylacetate, ethyleneglycol and mixtures.

14. The method according to claim 2, wherein the absorber material is selected from cellulose, modified celluloses, polyvinylidene fluoride (PVDF).

15. The method according to claim 1, wherein in step iia), the filtration is proceed by using a filter, wherein the filter is selected from modified cellulose, polytetrafluoroethylene (PTFE), PVDF, polyamide, or wherein the pore size of the filter is below 1 μm.

16. The method according to claim 1, wherein the reagent in step ix) is a compound of Xanthene-group, which is a compound of formula (II)

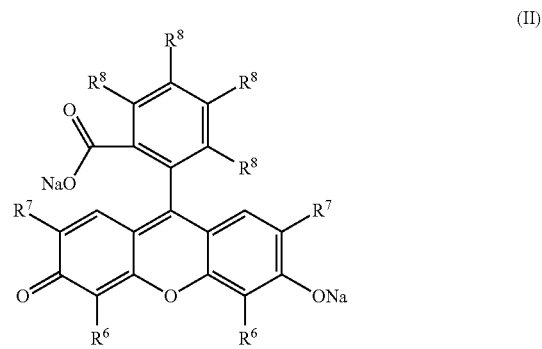

wherein $R^6$ and $R^8$ are independently from each other H or halogen;
$R^7$ is selected from H, halogen and $NO_2$.

17. The method according to claim 1, wherein the reagent in step ix) is a compound of formula (II),

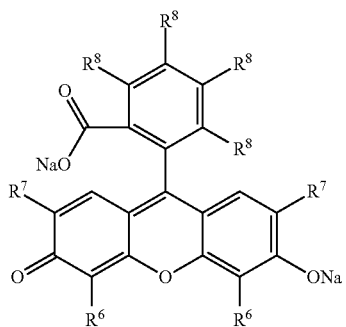 (II)

wherein
$R^6$ is iodine,
$R^7$ is iodine,
$R^8$ is chlorine.

18. The method according to claim 1, wherein $R^1$ in formula (I) has 16 to 20 carbon atoms, or wherein $R^1$ in formula (I) is a saturated straight chain hydrocarbon group or an unsaturated straight chain hydrocarbon group having 1, 2 or 3 C=C double bonds, wherein $R^1$ is an oleyl group ($C_{18}H_{35}$).

19. The method according to claim 1, wherein in step viii), the pH-value of the obtained extract of step vii) is adjusted to 1.8 to 3.5.

20. A use of the absorber material defined in claim 1, for the detection of the at least one organic amine of the formula (I), $$R^1-(NR^3R^2)_n-NR^4R^5 \quad (I),$$

wherein
n is 0, 1, 2, 3 or 4,
$R^1$ is a linear or branched, acyclic hydrocarbon group having 12 to 22 carbon atoms,
$R^2$ is $C_1$-$C_4$-alkanediyl,
$R^3$, $R^4$, $R^5$ are independently H or $C_1$-$C_4$ alkyl or —$(C_mH_{2m-2}O)p$-H, wherein m is 1, 2, 3, or 4 and p is =1, 2, 3 or 4.

21. Kit of parts comprising, as separate components,
A) the absorber material, as defined in claim 2,
B) a solvent a) selected from mixtures of at least one water-miscible organic solvent with water,
C) a solvent b) selected from mixtures of water with at least one water-miscible organic solvent in a weight ratio of 70:30 to 90:10,
D) a reagent, which is a compound of Xanthene-group, for combined use.

* * * * *

UNITED STATES PATENT AND TRADEMARK OFFICE
CERTIFICATE OF CORRECTION

| | |
|---|---|
| PATENT NO. | : 11,320,383 B2 |
| APPLICATION NO. | : 16/497801 |
| DATED | : May 3, 2022 |
| INVENTOR(S) | : Julia Jasper et al. |

It is certified that error appears in the above-identified patent and that said Letters Patent is hereby corrected as shown below:

In the Claims

At Column 16, Claim 1 should read as follows:

1. A method of determining whether a water- or steam-contacted surface of a water cycle or steam cycle contains a protective amount of at least one film forming organic amine of formula (I) having at least one linear or branched, acyclic hydrocarbon group having 12 to 22 carbon atoms, $$R^1\text{-}(NR^3R^2)_n\text{-}NR^4R^5 \quad (I)$$

wherein
  n is 0, 1, 2, 3 or 4,
  $R^1$ is a linear or branched, acyclic hydrocarbon group having 12 to 22 carbon atoms,
  $R^2$ is $C_1$-$C_4$-alkanediyl,
  $R^3$, $R^4$, $R^5$ are independently H or $C_1$-$C_4$ alkyl or -$(C_mH_{2m-2}O)p$-H, wherein m is 1, 2, 3, or 4 and p is = 1, 2, 3 or 4,
  the method comprising:
  an sampling step, wherein the surface is wiped with an absorber material, the organic amine is transferred to the absorber material, and the organic amine is taken from the surface,
  an extraction step, wherein a solvent is brought into contact with the absorber material and the organic amine is extracted into the solvent to obtain an extract containing the solvent and the organic amine, and
  an analysis step, analyzing the organic amine in the extract containing the solvent and the organic amine,
  on surfaces comprising the following steps:
  vi) transfer of the at least one organic amine of the formula (I) from the water- or steam-contacted surface of a water cycle or steam cycle to the absorber material, which comprises a solvent a),
  vii) extraction of the amine of the formula (I) out of the absorber material with a second solvent b), which is the same as or different from the solvent a) to obtain an extract comprising the solvent b), the at least one organic amine of the formula (I) and optionally the solvent a), Signed and Sealed this
Tenth Day of January, 2023

Katherine Kelly Vidal
*Director of the United States Patent and Trademark Office* iia) filtration of the extract,
viii) optionally, adjusting the pH-value of the obtained extract,
ix) adding a reagent capable to form a colored complex with the at least one organic amine of the formula (I),
x) detecting the colored complex.